United States Patent
Klatz et al.

[11] Patent Number: 5,913,885
[45] Date of Patent: *Jun. 22, 1999

[54] BRAIN COOLING DEVICE AND METHOD FOR COOLING

[75] Inventors: Ronald M. Klatz; Robert M. Goldman, both of Chicago, Ill.

[73] Assignee: Life Science Holdings, Inc., Chicago, Ill.

[*] Notice: This patent is subject to a terminal disclaimer.

[21] Appl. No.: 08/447,812

[22] Filed: May 23, 1995

Related U.S. Application Data

[63] Continuation of application No. 08/117,417, Sep. 7, 1993, abandoned, which is a continuation of application No. 07/704,038, May 22, 1991, Pat. No. 5,261,399.

[51] Int. Cl.⁶ ........................................................ A61F 7/10
[52] U.S. Cl. ............................ 607/104; 607/109; 607/110
[58] Field of Search ................................ 607/104, 107, 607/108–110; 165/46; 383/901

[56] References Cited

U.S. PATENT DOCUMENTS

| | | |
|---|---|---|
| 2,521,780 | 9/1950 | Dodd . |
| 3,463,161 | 8/1969 | Andrassy . |
| 3,606,890 | 9/1971 | Gilbert . |
| 3,871,381 | 3/1975 | Roslonski . |
| 3,908,655 | 9/1975 | Lund . |
| 4,138,743 | 2/1979 | Elkins et al. . |
| 4,382,446 | 5/1983 | Truelock et al. . |
| 4,552,149 | 11/1985 | Tatsuki . |
| 4,691,762 | 9/1987 | Elkins et al. . |
| 4,750,493 | 6/1988 | Brader . |
| 4,753,242 | 6/1988 | Saggers . |
| 4,765,338 | 8/1988 | Turner et al. . |
| 4,869,250 | 9/1989 | Bitterly . |
| 4,920,963 | 5/1990 | Brader . |
| 5,163,425 | 11/1992 | Nambu et al. . |
| 5,261,399 | 11/1993 | Klatz et al. . |

FOREIGN PATENT DOCUMENTS

| | | |
|---|---|---|
| 8607793 | 1/1987 | Germany . |
| 9000752 | 10/1991 | Netherlands . |
| 446015 | 11/1974 | U.S.S.R. . |
| 454907 | 7/1975 | U.S.S.R. . |
| 652942 | 3/1979 | U.S.S.R. . |
| 904695 | 2/1982 | U.S.S.R. . |
| 1138152 | 2/1985 | U.S.S.R. . |
| 2130489 | 6/1984 | United Kingdom . |
| 82/04184 | 12/1982 | WIPO . |
| 89/09583 | 10/1989 | WIPO . |

*Primary Examiner*—Mark S. Graham
*Attorney, Agent, or Firm*—Oliff & Berridge, PLC

[57] ABSTRACT

This invention discloses a device and a method for resuscitating the brain as result of ischemic and anoxic injuries whereby the patient survives neurologically intact. The device includes a head enveloping helmet and neck supporting back plate with interconnected hollow cavities to allow chilled fluid from an activated coolant source to pass therethrough and subsequently chill the brain and upper spinal column. Once chilled, the brain's metabolism is slowed whereby resuscitation efforts can continue while neurologic damage is minimized. The method includes placing and adjusting the helmet on the patient's head, placing the back plate under the patient's neck and into abutment with the helmet, connecting the helmet to the coolant source and activating the coolant source.

56 Claims, 8 Drawing Sheets

BRAIN COOLING DEVICE AND METHOD FOR COOLING

CROSS REFERENCES TO RELATED APPLICATIONS

This application is a continuation of application Ser. No. 08/117,417 filed on Sep. 7, 1993, abandoned, which is a continuation of application Ser. No. 07/704,038 filed on May 22, 1991, now U.S. Pat. No. 5,261,399.

FIELD OF THE INVENTION

The present invention relates generally to treating ischemic and anoxic brain injuries. More particularly, the present invention provides an apparatus and method for cooling of the brain and maintaining it at a temperature below normal body temperature during trauma or others periods of decreased blood flow. With the present inventions the brain and associated neurologic tissues survive the anoxic or ischemic trauma intact. The victim recovers with increased chances of survival and less chance of permanent brain damage.

BRIEF DESCRIPTION OF THE PRIOR ART

When an ischemic or anoxic injury occurs, the brain is deprived of freshly oxygenated blood. For example, this situation typically occurs during cardiac arrest, respiratory arrest, stroke and other cerebrovascular trauma, suffocation, drowning, strangulation, electrocution, toxic poisoning (carbon monoxide, cyanide, etc.), metabolic insults or other similar trauma. Without a steady supply of freshly oxygenated bloods the brain ceases to function and after resuscitation, most patients will suffer some damage to the brain and associated neurologic tissues.

For example, among cardiac arrest victims overall less than 10% survive neurologically intact and without significant brain damage. The other approximately 90% either die or sustain some neurologic injury from ischemia, (i.e., lack of blood flow to the brain), or anoxia (i.e., lack of oxygen to the brain). Such frequency of neurologic injury occurs because after a cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving the brain in addition to resuscitating the heart.

As indicated above, anoxic and ischemic brain injuries from cardiac arrest result in damage to the brain and associated neurologic tissues after about four minutes. In contrast, the heart can survive intact up to four hours after cardiac arrest. The short viability of brain tissue upon deprivation of oxygenated blood is a result of the requirement of high amounts of nutrients for tissue maintenance. Brain tissue uses almost all of the nutrients supplied by the circulating blood for maintenance and has very little remaining for storage. Absent blood flow to the brain, the small amount of stored nutrients is rapidly exhausted. Once exhausted, brain oxygen content rapidly depletes. This oxygen depletion is traumatic and causes a series of reactions in the oxygen starved brain tissue cells. These reactions are believed to produce free radical ions, primarily consisting of the superoxide radical $O_2^-$. These free radicals complex with proteins in the brain and associated neurologic tissues, altering respiration, energy transfer and other vital cellular functions, and irreversibly damaging these tissues.

Efforts should be directed toward resuscitating the brain to attempt to extend the period of time the brain can function without oxygen while the patient remains neurologically intact. The medical literature is replete with examples of humans surviving extended periods of time (greater than 5 minutes) without oxygen being delivered to the brain.

Hypothermic therapy is one method of keeping the brain alive absent oxygen. It involves cooling the brain to a temperature where its metabolic activity is decreased. When the brain's metabolic activity is decreased, it uses much less oxygen and stored nutrients are exhausted slowly, while production of irreversibly damaging $O_2^-$ free radicals is slowed and almost completely ceased. Thus, upon resuscitating the body from trauma, the patient emerges neurologically intact. For example, children revived after hours of submersion in very cold water have fully recovered with little if any neurologic damage.

Cooling for hypothermic therapy is presently achieved by either cold room technology involving a heat exchanger in a heart-lung bypass. The surgery involved with the cold room technology takes place in a room the size of a meat locker or large commercial freezer. Cooling is also achieved by traditional devices such as natural or synthetic ice packs. Both of these devices and methods have several drawbacks.

A major drawback with the cold room technology is that it is invasive and quite expensive. It involves a team of highly trained, skilled medical personnel to operate and supervise a standard heart-lung bypass machine. This technology is not portable as it is restricted to a surgical operating room setting. Also, cooling is progressive, not instantaneous. Natural or synthetic ice packs, although portable and non-invasive are disadvantageous because they are messy and do not rapidly achieve the low temperatures required to hypothermically shock the brain. Additionally, ice packs are ineffective in extremely hot environments such as deserts because they melt rapidly.

OBJECTS OF THE INVENTION

It is therefore an object of this invention to non-invasively treat ischemic and anoxic brain injuries promptly upon cardiac arrest whereby resuscitation efforts are applied in time for a patient to survive neurologically intact. By directing resuscitation efforts to treat the brain promptly the present invention allows medical personnel substantial additional time (beyond the critical four minute window) to regain the failed heart's circulation without the patient suffering permanent neurologic damage.

It is therefore an object of this invention to provide a method for treating anoxic or ischemic injuries to the brain whereby the patient survives neurologically intact.

It is also an object of the invention to provide a method of treating ischemic and anoxic brain injuries so as to inhibit free radical chemical species from complexing with proteins in the brain and neurologic tissue to avoid permanent irreversible damage.

It is also an object of the invention to non-invasively treat ischemic and anoxic brain injuries.

It is a further object of the invention to provide an apparatus which can substantially instantaneously cool the brain to a temperature where brain metabolism is slowed.

It is a further object of the invention to provide a portable apparatus for non-invasively treating anoxic and ischemic brain injuries which can substantially instantaneously cool the brain and associated neurologic tissue.

It is a further object of the invention to provide an apparatus for treating the aforementioned injuries by instantaneously cooling the brain, associated neurologic tissues and the upper spinal column.

It is further an object of the invention to provide an apparatus for treating the aforementioned injuries, which is suited for field as well as clinical use and that can be operated by a single person with minimal medical training and experience.

It is a still further object to provide apparatus for cooling the brain which has very few parts and is economical to manufacture and easy to use.

Other objects and advantages of the present invention will be apparent to those skilled in the art from the following description and the appended claims.

SUMMARY OF THE INVENTION

The present invention focuses on initial resuscitation efforts toward resuscitating the brain due to its short viability, rather than the heart. The invention includes a non-invasive method which inhibits neurologic damage and resulting ischemic and anoxic injury on cardiac arrest. The method includes placing and adjusting a scalp-enveloping helmet provided with means therein for circulation of a coolant fluid and circulating within said member a coolant fluid so as to lower the temperature of the patient's brain over the patient's head. In a particular preferred embodiment, substantially simultaneously with the circulation of coolant fluid through the scalp-enveloping helmet a neck supporting back plate shaped to correspond with the natural curvature of the neck is put in place to support the patient's neck in upward positions, the coolant fluid also circulates through the back plates.

The present invention also provides novel apparatus for alleviating ischmic and anoxic brain injuries in a cardiac arrest mammal. The apparatus of the invention provides in combination, a helmet-like scalp-enveloping element provided with means therein for circulation of a coolant fluid. The scalp-enveloping element is provided with inlet means for receiving a coolant fluid from a coolant fluid source to which it is operatively connected. Outlets are also provided in the scalp-enveloping element to permit the discharge therefrom of coolant fluid after circulation through the element. A particularly preferred apparatus also includes a neck supporting back plate shaped to correspond with the natural curvature of the patient's neck. The neck supporting back plate is also provided with means therein to permit passage of coolant fluid therethrough. Means are provided to allow for fluid communication between the scalp-enveloping element and the neck supporting back plate so that coolant fluid can be circulated through both pieces.

DETAILED DESCRIPTION OF THE INVENTION

Figure 1:
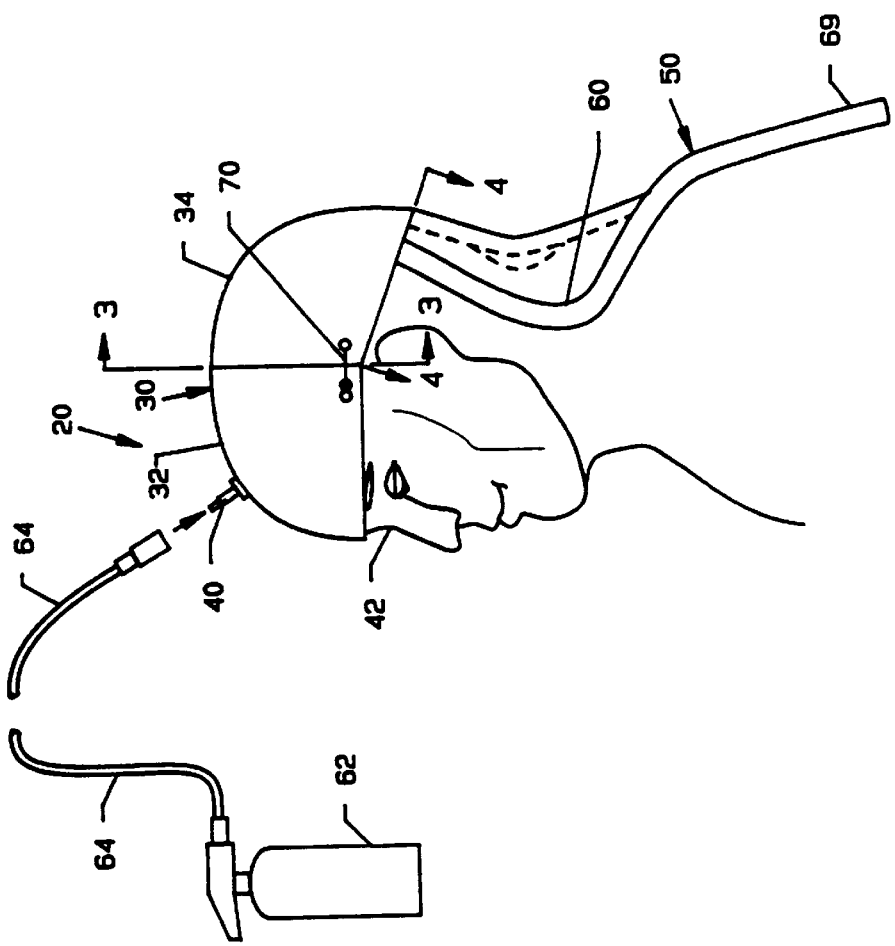
FIG. 1 is a side view of the brain cooling device of the present invention.

Referring to FIG. 1, this embodiment of the brain cooling device 20 includes an adjustable multiple piece scalp-enveloping element or helmet 30, a back plate 50 and a coolant source 62. All of these components are designed to cooperatingly fit together. These components are lightweight and portable. They can be easily and quickly assembled together immediately prior to use at the cite of the trauma. Detachment is also simple and quick.

Figure 2:
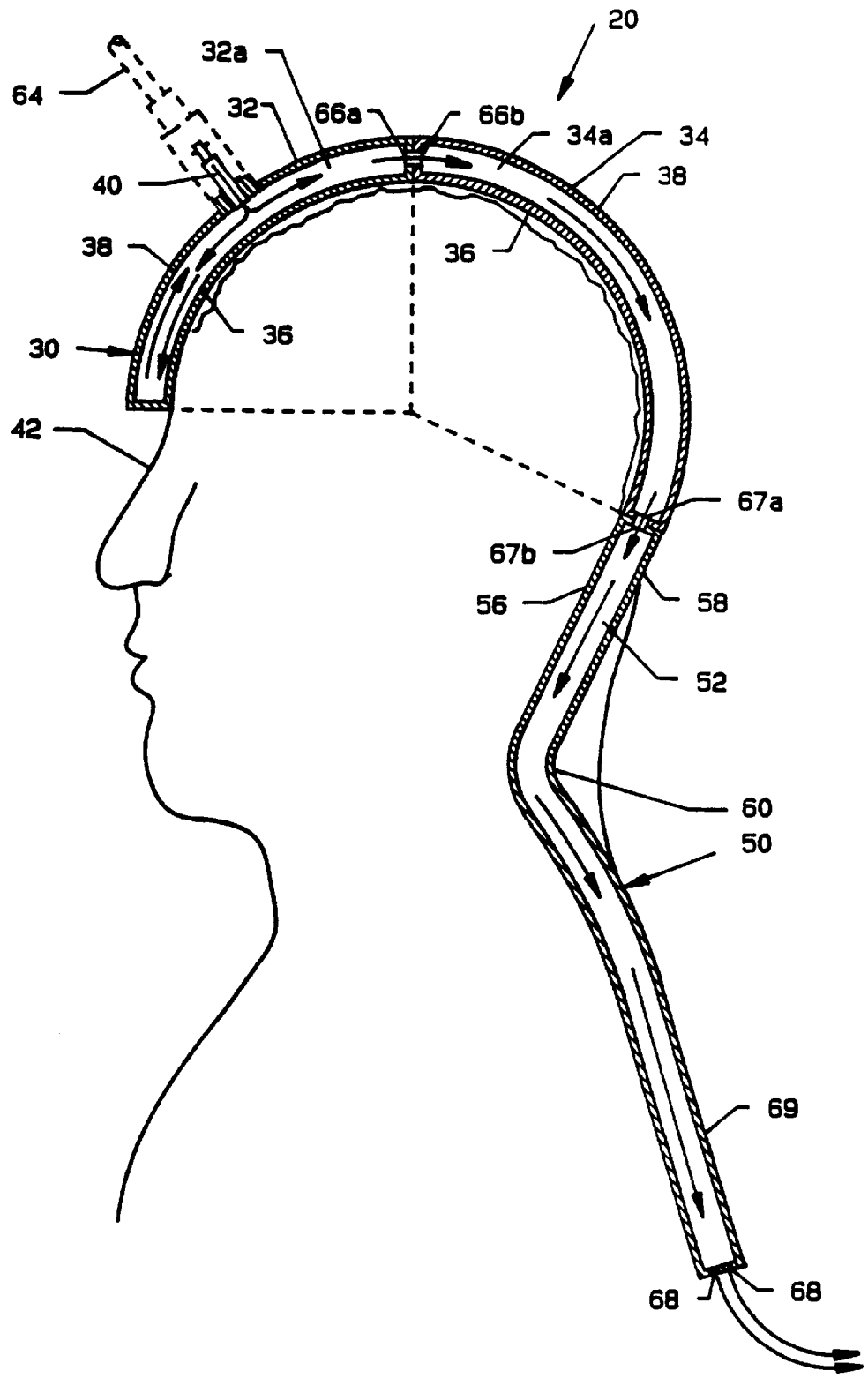
FIG. 2 is a cross sectional view of the brain cooling device of the present invention.

The scalp-enveloping element or helmet 30 is of a universal size to insure conformity to all head sizes. While a two piece construction is preferred, one-piece or multiple piece helmets are also possible. Each helmet piece 32, 34 has a hollow cavity 32a, 34a between the inner shell 36 and the outer shell 38 (FIG. 2). The helmet 30 includes flexible adjustment mechanisms 70 on both sides with cooperating coupling elements on each piece (or segment with one-piece helmets) enabling conformity to all head sizes. The front piece 32 of the helmet 30 has at least one outwardly extending nipple 40 to receive coolants which enters this front piece 32 into the hollow cavity 32a, whereby coolant circulates throughout all of the hollow cavities 32a, 34a, 52 (see FIG. 2) in each helmet piece 32, 34 and in the back plate 50, cooling the inner shell 36 (FIG. 2) of the helmet 30. The chill penetrates the inner shell 36 (FIG. 2) to contact the patient's head 42 at a temperature sufficiently low to quickly slow the brain's metabolism and inhibit potential neurologic damage.

The back plate 50 is preferably a one piece unit, although multiple piece construction is also permissible. Like the helmet pieces 32, 34, the back plate 50 has a large hollow cavity 52 between the inner shell 56 and the outer shell 58 (FIG. 2). This back plate 50 supports the neck and permits additional cooling of the brain stem and upper spinal column. The back plate 50 can be maintained in fluid connection with the helmet 30 by body weight alone in an abutment relationship. However, fastening means such as buckles, straps, tape, snaps, rods, snap-together molding or other suitable fasteners can be used. Preferably, this back plate 50 is saddle shaped at its upper portion 60 to accommodate and exaggerate the natural curvature of the neck, hyperextending it, while positioning it upwards. In this positions the carotid arteries or other large neck vessels are exposed and easily accessible for catherization involved with other resuscitation methods.

The coolant source 62 is preferably a compressed liquid such as carbon dioxides which upon decompression becomes a cold gas. Prior to activations these cold compressed liquids are preferably stored in portable containers such as tanks. Other suitable compressed liquids are freon or nitrogen. Alternately, very cold liquids such as supercooled water, self freezing gel, packed liquid, ice water, or other such chemicals may be passed into the helmet through a tube 64 operatively connected to the nipple 40.

An additional alternative coolant involves materials within the hollow cavities of the helmet, the back plate, or both which chill upon activation when use is desired. For example, the helmet, back plates or both could be pre-filled with Ammonium Nitrate or equivalent thereof, which reacts endothermically when activated by water, chilling these pieces.

FIG. 2 is a cross sectional view of the helmet and back plate pieces of the first embodiment of the invention shown in FIG. 1. This view shows the coolant's circulation between these components in detail. The specific circulation path is shown by arrows.

Coolant fluid, consisting of gas or very cold liquid moves by expansion from the coolant source 62 through a tube 64 to the nipple 40 on the front piece 32 of the helmet 30. This nipple 40 is preferably located on the front piece 32 of the helmet 30 since its angular orientation away from the body provides easy tube accessibility. However, single or multiple nipples can be placed on any of the helmet 32, 34 or back plate 50 pieces. Coolant then enters the hollow cavity 32a in the front piece 32 of the helmet 30, and circulates throughout the hollow cavities 34a, 52 of the rear helmet 34 and back plate 50 pieces.

Figure 3:
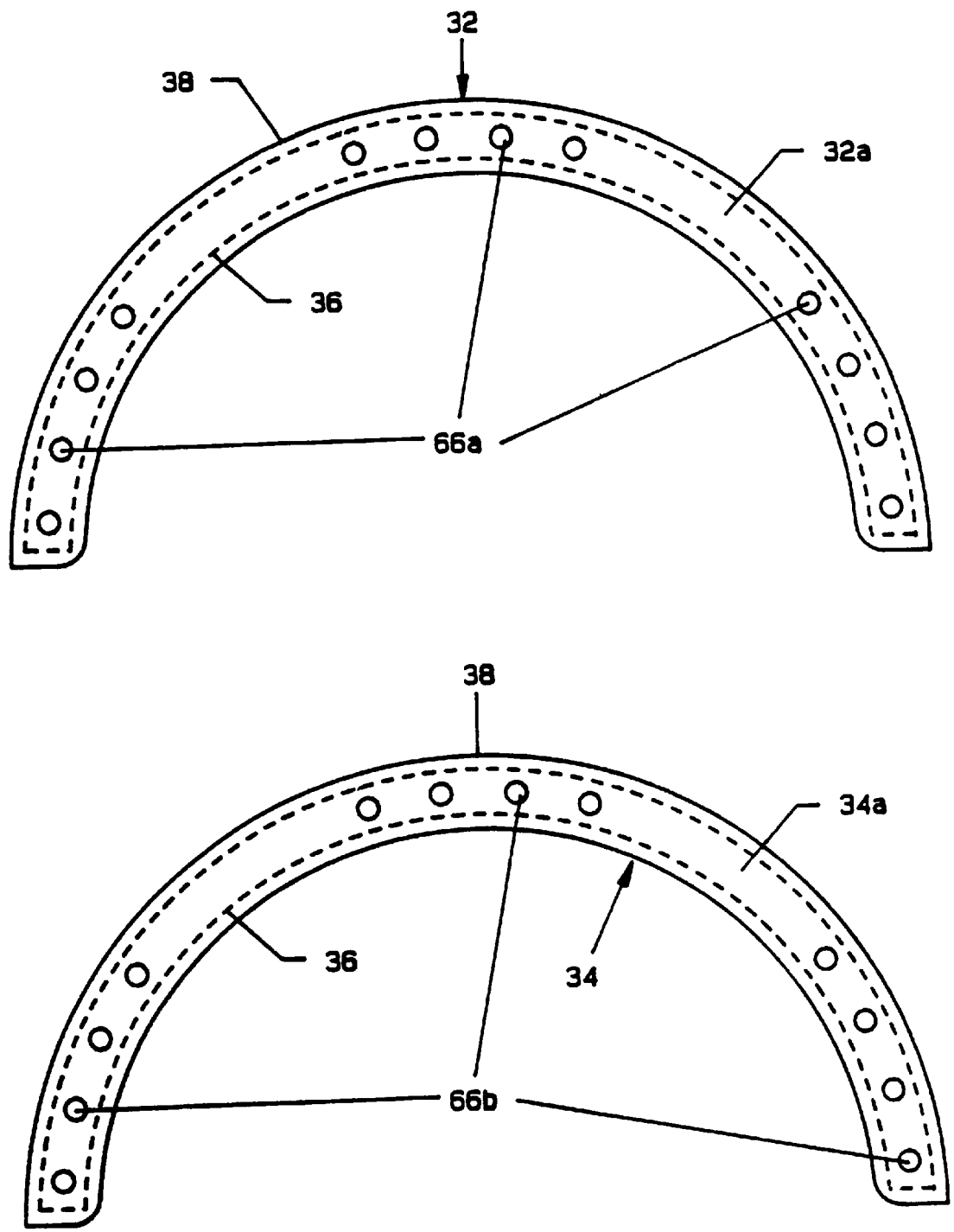
FIG. 3 is a cross sectional view of the interface of the front and rear helmet pieces taken along line 3—3 of FIG. 1.
Figure 4:
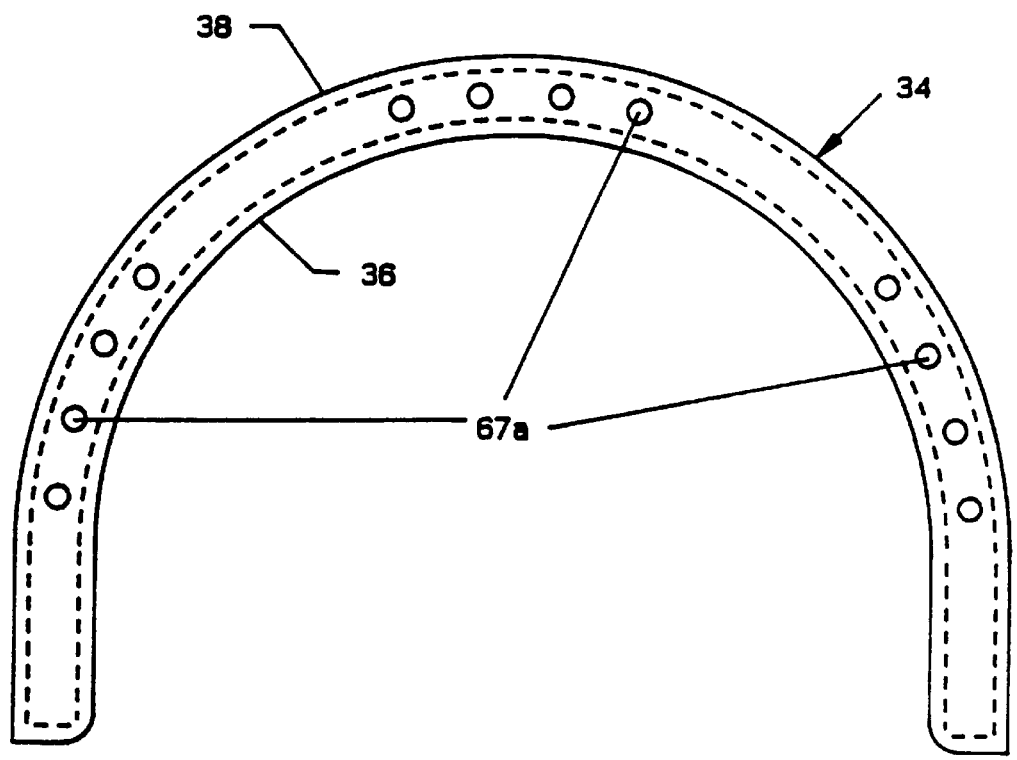
FIG. 4 is a cross sectional view of the interface between the rear helmet and back plate pieces taken along line 4—4 of FIG. 1.
Figure 4:
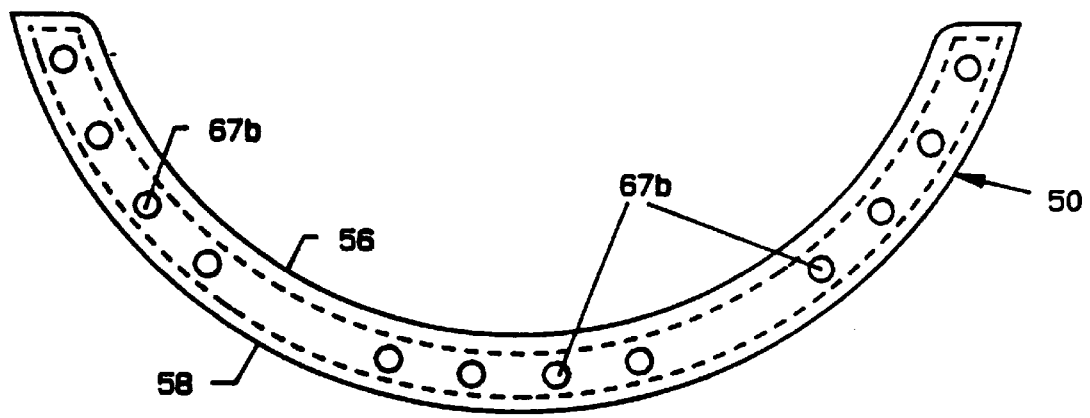

Coolant circulates throughout the helmet 32, 34 and back plate 50 pieces through cooperatively aligned circulation ports 66a, 66b, 67a, 67b located on the respective ends of each helmet 32, 34 and back plate 50 piece. FIG. 3 shows these cooperatingly aligned circulation ports 66a, 66b at the interface of the front 32 and rear 34 helmet pieces respectively, while FIG. 4 shows these cooperatingly aligned circulation ports 67a, 67b at the interface of the rear helmet 34 and the back plate 50 pieces. The outer and inner shells between the hollow cavities in these helmet and back plate pieces is shown in phantom. While the illustrated port arrangement is preferred, any alternate arrangement is also permissible provided this arrangement permits chilled fluid to circulate throughout the helmet 30 and the back plate 50.

Coolant exits the system through exhaust ports 68, in the lower portion 69 of the back plate 50. Additional exhaust ports may also be located on the helmet pieces to accommodate possible increased pressure. These exhaust ports would aid in eliminating any potential pressure build up in the hollow chambers which might damage the helmet 32, 34 or the back plate 50 pieces.

The preferred helmet 32, 34 and back plate 50 pieces are made of a polymeric material such as blow molded plastics, nylon, fiberglass, rubber, metal or the like. This polymeric material is able to withstand contraction from rapid cooling and subsequent expansion upon warming without cracking. The inner helmet shell 36 is thin enough to conduct the chill from the hollow cavities 32a, 34a, 52 to the brain at a temperature sufficiently low enough to quickly slow brain metabolism, and inhibit potential neurologic damage. The inner helmet shell 36 is also thick and tough enough to support the patient's head 42 without deforming when the helmet is adjusted and placed on the patient's head 42. However, soft shell or cloth-like helmets or helmet segments are also permissible provided they have a hollow cavity which can sufficiently receive and circulate coolant fluid.

Padding (not shown) may also be included on the inner helmet shell 36 and back plate inner shell 56 for additional comfort. However, this padding should be of a material such as sponge or the like which allows the chill to quickly reach the brain.

Figure 5A:
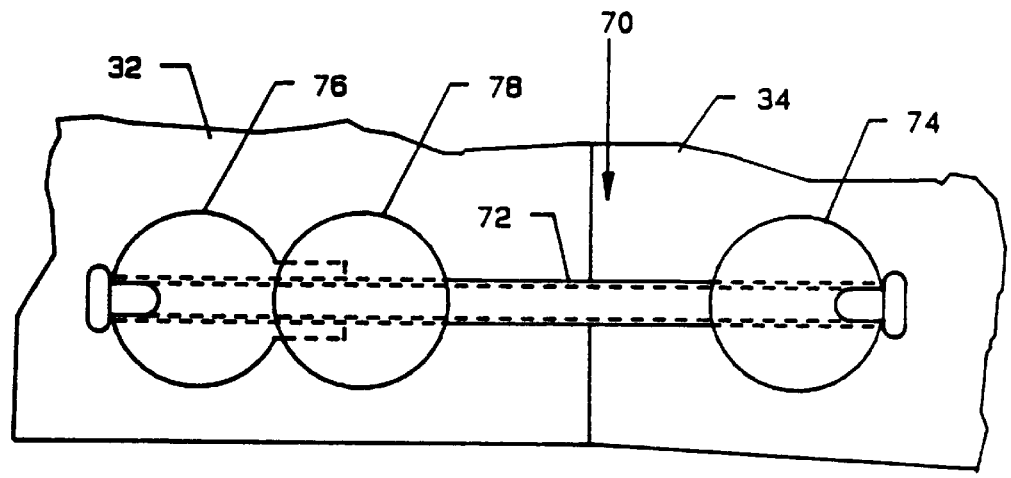
FIGS. 5A and 5B are side and top partial sectional views of the helmet adjustment mechanism.
Figure 5B:
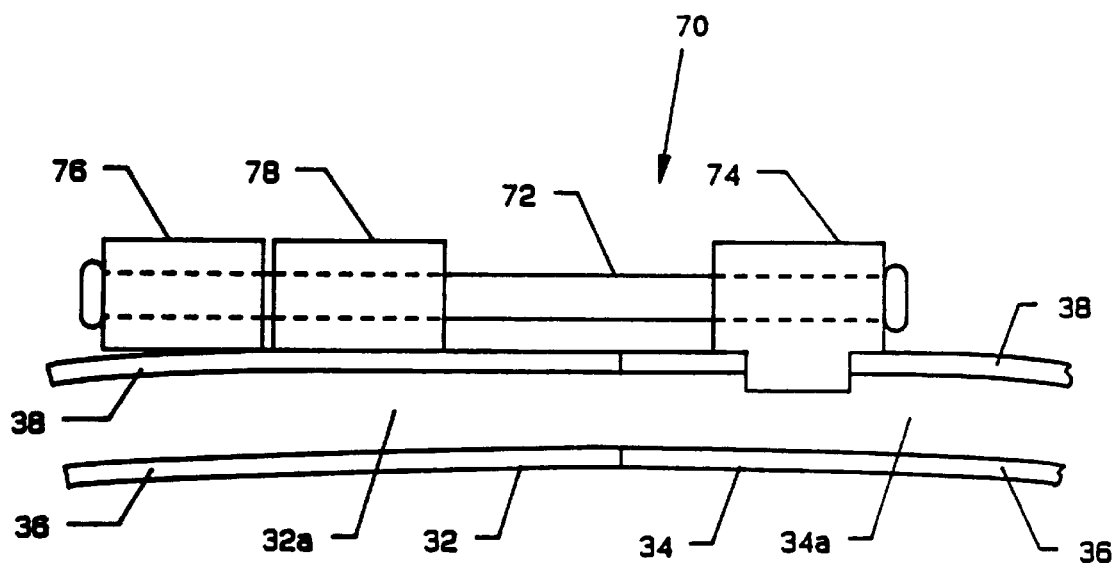

FIGS. 5A and 5B show the adjustment and attachment mechanisms 70 for the helmet pieces 32, 34. The preferred elements include flexible tension straps 72 permanently mounted in a first anchor 74, affixed to the outer helmet shell 38 and mounted in freely moving latch handles 76. These flexible tension straps 72 are elastic enough to allow for adjustment to various head sizes, yet resilient enough to maintain the helmet's compression fit on the patient's head 42. A first anchor 74 is permanently affixed to the outer shell 38 of the rear helmet piece 34 while the latch handle 76 is free and mounts at a point forward of a second anchor 78. This second anchor 78 is permanently affixed to the outer shell 38 on the front piece 32 of the helmet 30, and accommodates the flexible tension strap 72 through its center as the latch handle 76 abuts the second anchor 78 upon securement. While this arrangement between the latch handle 76 and anchors 74, 78 is preferred, the opposite arrangement of a permanently affixed anchor to the front helmet piece, including the permanently mounted flexible tension strap and a permanently affixed anchor to the rear helmet piece, is also permissible. Alternately, the helmet pieces can be held together by straps, buckles, tape, manual compression, or other similar attachment devices.

While this first embodiment is preferably a three piece unit (two helmet pieces and a back plate piece) the brain cooling device is also effective with only a front helmet piece which has been activated with coolant and is manually pressed against the head. This is also true for the other helmet piece(s) and the back plate or pieces thereof, which can also function separately if equipped with nipples or other suitable means and attached to coolant sources.

This embodiment of the brain cooling device is relatively small. It is portables can be fitted into a suitcase-like carrying cases and is suitable for field use, such as in ambulances, battlefields, athletic fields, aircraft, marine vehicles, spacecraft, emergency treatment facilities, and the like. It is lightweight and can be carried directly to the patient. In one examples the brain cooling device fits in a suitable carrying case and weighs approximately thirteen pounds.

Figure 6:
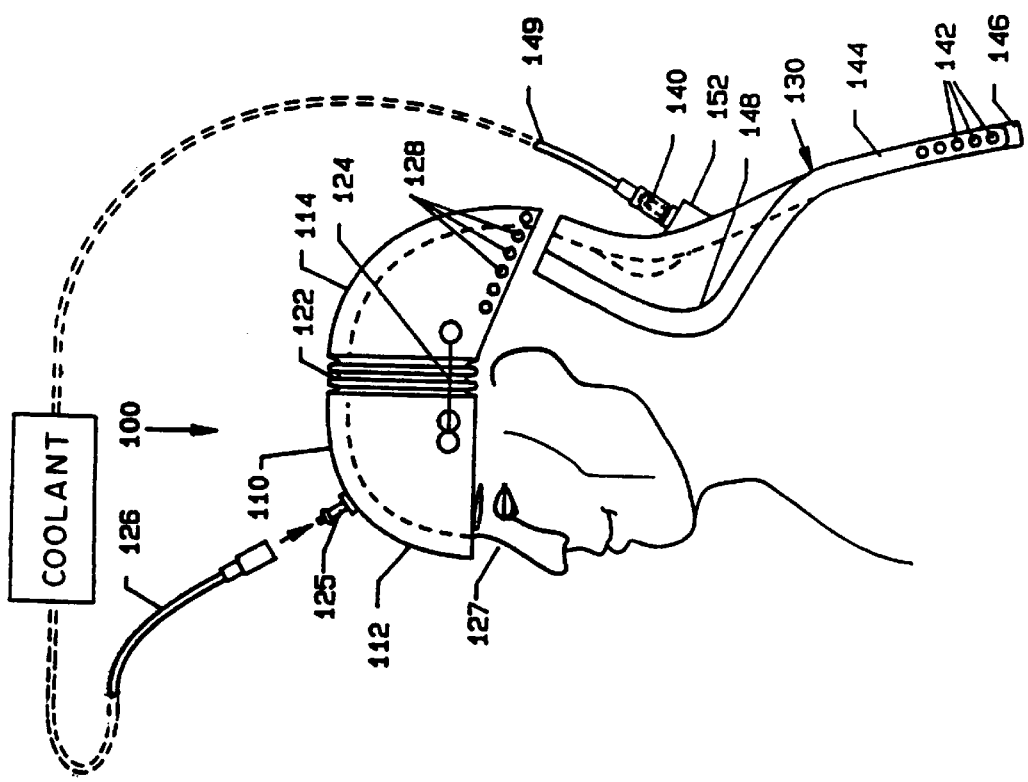
FIG. 6 is a side view of a second embodiment of the brain cooling device of the present invention.

FIG. 6 is a second embodiment of the brain cooling device 100. This embodiment is made of two pieces: a one piece helmet 110 with front and rear segments 112, 114 in combination with a back plate 130. Both the helmet 110 and the back plate 130 are operatively connected to coolant sources. The coolant sources employed with this embodiment are similar to those disclosed above in the first preferred embodiments. Like the first preferred embodiment these components are lightweight and portable. They can be easily and quickly assembled together immediately prior to use at the cite of the trauma. Detachment is simple and quick. Although these components are designed to operate as a unit, either the helmet 110 or the back plate 130 can be used separately should it be necessitated or desired.

Figure 7:
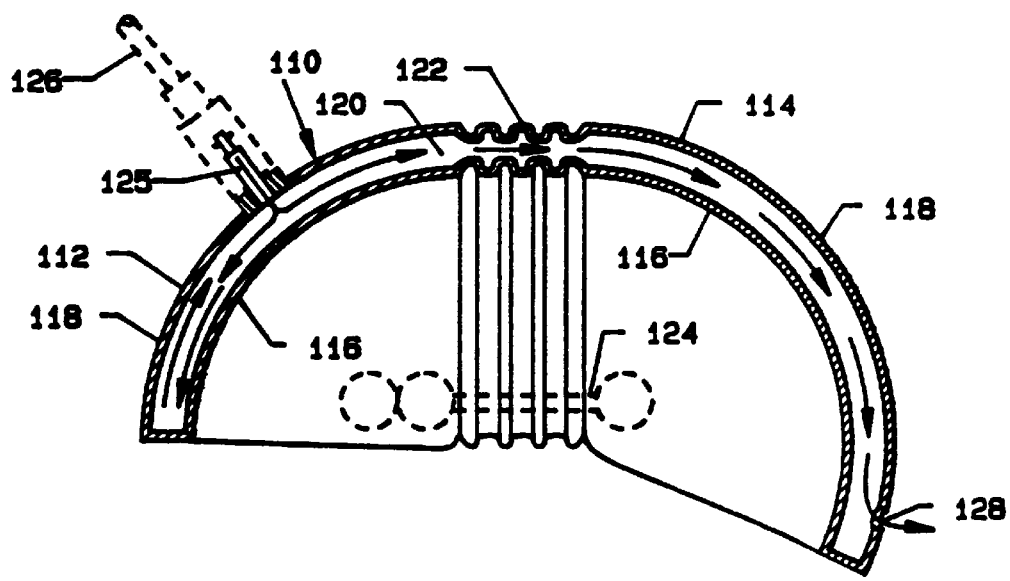
FIG. 7 is a cross sectional view of the embodiment of the brain cooling device shown in FIG. 6.

The preferred helmet 110 is of a universal size to insure conformity to all head sizes. The helmet has inner 116 and outer 118 shells with a cavity 120 therebetween (FIG. 7). The two helmet segments 112, 114 separated by a side-to-side baffled connector 122. This baffled connector 122 is of an elastomeric or other suitable flexible material with several folds on both shells. This baffled connector 122 allows the helmet 110 to be adjusted to various head sizes. While a side-to-side connection is preferred, a front to rear connection is also permissible. While baffled or folded connectors are preferred, other flexible, resilient, elastomeric connectors are also suitable. Also, while two helmet segments 112, 114 are preferred, additional segments are also permissible provided these segments are separated by baffled or other suitable connectors. Flexible adjustment mechanisms 124, preferably on both sides of the helmet 110 provide further adjustability. These adjustment mechanisms are identical to those disclosed for the preferred embodiment and are illustrated in FIG. 5.

The front helmet segment 112 has at least one outwardly extending nipple 125 to receive coolant from a tube 126. The nipple 125 in the front helmet segment 112 extends into the hollow cavity 120 for circulating coolant throughout the entire hollow cavity 120 (see FIG. 7), cooling the inner shell 116 of the helmet 110. The chill penetrates the inner shell 116 to contact the patient's head 127 at a temperature sufficiently low to quickly slow the brain's metabolism and inhibit potential neurologic damage. The helmet 110 also includes exhaust ports 128 at its lower end to allow coolant to leave the helmet 110 and equalize pressure, whereby, the helmet 110 does not crack or sustain other damage.

Figure 8:
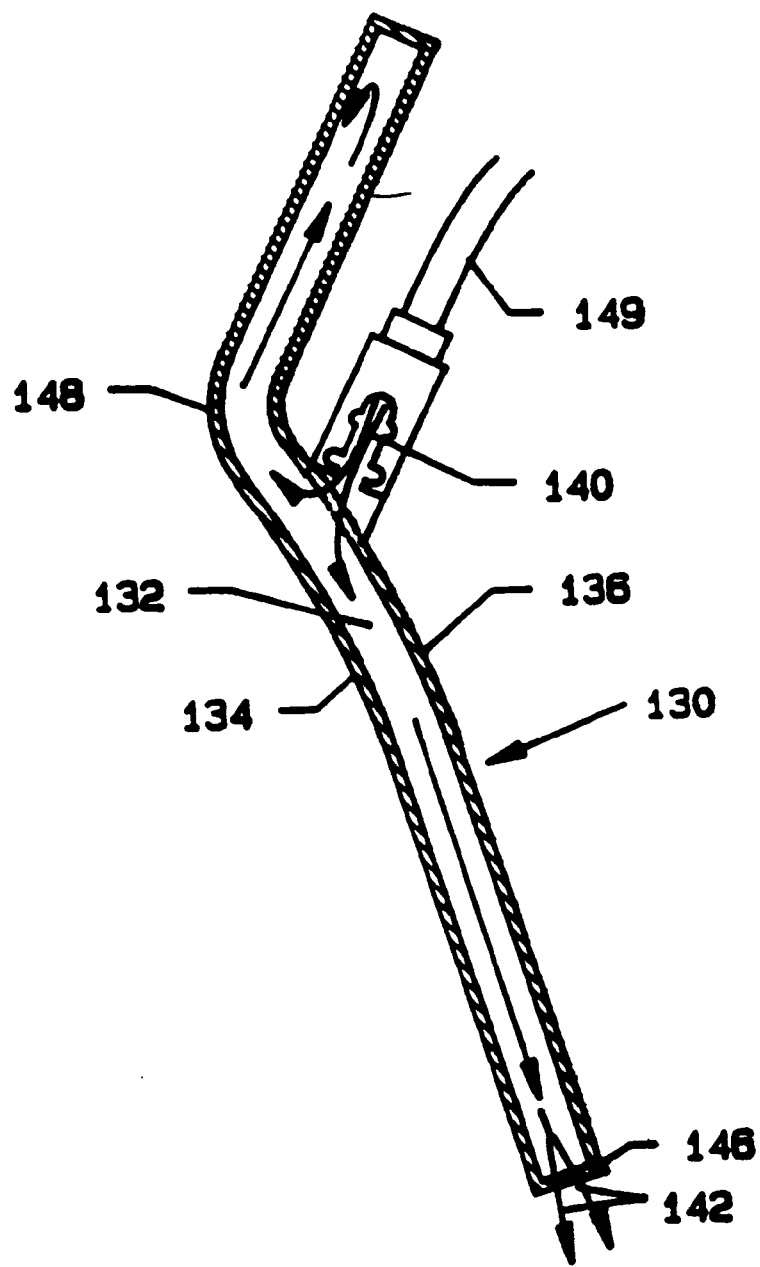
FIG. 8 is a cross sectional view of the back plate of the embodiment of the brain cooling device shown in FIG. 6.

The back plate 130 provides additional cooling for the brain stem and upper spinal column. It is preferably a one piece unit, although multiple piece construction is permissible. Like the helmet 110, the back plate 130 has a large hollow cavity 132 between the inner shell 134 and outer shell 136 (FIG. 8). The back plate 130 is separate from the helmet 110 during use. The back plate 130 includes a centrally positioned nipple 140 to receive coolant. Single or multiple nipples placed at other locations on this back plate or any pieces thereof, are also permissible. The back plate 130 includes exhaust ports 142 along the perimeter 144 of the back plate's lower portion 146 to allow coolant to leave, equalizing pressure in the cavity 132 to prevent damage to the back plate 130, such as cracking. Additional or substitute exhaust ports can be placed anywhere on the back plate.

Like the preferred embodiment, this back plate 130 supports the neck. It has a saddle shaped upper portion 148 to accommodate and exaggerate the natural curvature of the neck, hyperextending it, while positioning it upwards. In this position, the carotid arteries or other large neck vessels are exposed and easily accessible for catherization involved with other resuscitation methods.

FIG. 7 is a cross sectional view of the helmet of this second embodiment. This view shows the coolant's circulation between the helmet segments 112, 114 in detail. The specific circulation path is shown by arrows.

Coolant fluid, consisting of gas at a low temperature or very cold liquid moves by expansion from the coolant source (not shown) through a tube 126 operatively connected to the nipple 125 on the front segment 112 of the helmet 110. This nipple 125 is preferably located on the front segment 112 of the helmet 110 since its angular orientation away from the body provides ease tube accessibility. However, single or multiple nipples can be placed on any of the helmet segments 112, 114. Coolant then enters the hollow cavity 120 in front helmet segment 112, and circulates through the baffled connector 122 to the rear helmet segment 114. Coolant exits the system through exhaust ports 128, preferably located on the lower portion of the rear helmet segment 114. Additional or substitute exhaust ports may also be located anywhere on any of the helmet segments to accommodate possible increased pressure.

FIG. 8 is a cross sectional view of the back plate 130 of this second embodiment. This view shows the coolant's circulation within this back plate's hollow cavity 132 between the inner and outer shells 116, 118 in detail. The circulation path is shown by arrows.

Similar to the helmet 110 the coolant fluid, consisting of gas or very cold liquid, moves by expansion from the coolant source (not shown) through a tube 149 to the nipple 140 on the bottom side 152 of the back plate 130. This nipple 140 is preferably centrally located on the curved upper portion 148 to provide easy tube accessibility. Coolant then enters the hollow cavity 132 and circulates throughout the entire back plate 130. Coolant exits the back plate 130 through the exhaust ports 142, preferably located on the perimeter 144 of the lower portion 146. Additional or substitute exhaust ports may also be located anywhere on this back plate 130 to accommodate possible increased pressure.

Similar to the first preferred embodiments the helmet 110 and back plate 130 of the embodiment are made of a polymeric material such as blow molded plastics, nylon, fiberglass, rubber, metal or the like. This polymeric material is able to withstand contraction from rapid cooling and subsequent expansion upon warming without cracking. The inner helmet shell 116 is thin enough to conduct the chill from the hollow cavity 120 to the brain at a temperature sufficiently low enough to quickly slow brain metabolism and inhibit potential neurologic damage. The inner helmet shell 116 is also thick and tough enough to support the head without deforming when the helmet 110 is adjusted and placed on the patient's head 127. However, soft shell or cloth-like helmets are also permissible provided they have a hollow cavity which can sufficiently receive and circulate coolant fluid.

Padding (not shown) may also be included on the helmet 116 and back plate 134 inner shells for additional comfort. However, this padding should be of a material such as sponge or the like which allows the chill to quickly reach the brain.

While these two preferred embodiments described in detail herein are portable devices particularly suited for field use, they are also suited for stationery, clinical use. Should a clinical device be desired, these two portable embodiments could be made larger and modified accordingly for such use.

In operation, the brain cooling apparatus of the invention sufficiently chills the brain to slow its metabolism allowing for continued resuscitation efforts. As previously stated, the invention comprises a method of treating anoxic and ischemic injuries suffered as a result of cardiac arrest, respiratory arrest, stroke or other cerebrovascular trauma, suffocation, drowning, electrocution, toxic poisioning (carbonmonoxide, cyanide, etc.) metabolic insults or other similar trauma.

Specifically, operation of the apparatus involves merely placing the patient on the back plate, attaching the helmet pieces (if using a multiple piece helmet), adjusting the helmet on the patient's head, attaching the helmet to the back plate, attaching a tube from the nipple(s) to the coolant source and activating the coolant source. This process is quite simple and can be performed at the trauma cite by a person with minimal, if any, medical training.

From the foregoing description, it is apparent that the objects of the present invention have been achieved. While only certain embodiments have been set forth, alternative embodiments and various modifications will be apparent to those skilled in the art. These and other alternatives and modifications are considered equivalents and within the spirit and scope of the present invention.

What is claimed is:

1. An apparatus for cooling a brain, comprising:
   a. means for enveloping a head, said head enveloping means for resting unsupported on the head, said head enveloping means including outer and inner shells with at least one cavity intermediate said outer and inner shells for receiving and permitting circulation and expansion of coolant fluid, said cavity including a plurality of valveless outlets for coolant fluid, said plurality of valveless outlets being disposed along a lower back edge portion of said enveloping means and providing communication between the cavity and the ambient atmosphere upon initial introduction of coolant fluid into the cavity;

b. an instantaneously activatable coolant fluid source; and c. means for providing fluid communication between said fluid source and said head enveloping means, whereby when said coolant fluid source is activated and coolant fluid is introduced into said head enveloping means, said head enveloping means becomes instantaneously chilled, to rapidly transmit this chill to the brain, cooling the brain to a temperature sufficient to slow the metabolism of the brain.

2. The apparatus of claim 1, wherein said head enveloping means includes a helmet-type element of multiple piece construction which includes flexible means for adjusting and retaining said helmet-type element on a patient's head.

3. The apparatus of claim 2, wherein said head enveloping means includes a multiple piece helmet-type element, each of said pieces including means therein for circulation of coolant fluid.

4. The apparatus of claim 3, wherein said means for circulation of coolant fluid includes cooperatively aligned ports at an interface of said helmet pieces.

5. The apparatus of claim 1, wherein said head enveloping means includes a helmet-type element of unitary construction which includes flexible means for adjusting and frictionally retaining said helmet-type element on a patient's head.

6. The apparatus of claim 1, additionally including neck supporting means for cooling the upper spinal column of the neck and back of a patient, said neck supporting means provided with means therein for circulation of coolant fluid, and means for providing fluid communication between said head enveloping means and said neck supporting means, said neck supporting means extending a substantial distance along the upper spinal column, whereby when said coolant fluid source is activated and coolant fluid is introduced into said neck supporting means, said neck supporting means becomes instantaneously chilled to rapidly transmit this chill to the upper spinal column at a temperature sufficient to slow the metabolism of the brain.

7. The apparatus of claim 2, wherein said neck supporting means includes ports cooperatively aligned with the plurality of valveless outlets of said head enveloping means.

8. The apparatus of claim 6, wherein said neck supporting means includes an upwardly curved portion to permit access to vessels of the neck.

9. The apparatus of claim 6, wherein said neck supporting means includes exhaust ports at a lower perimeter.

10. An apparatus for cooling a brain, comprising:

a. means for enveloping a head, said head enveloping means for resting unsupported on the head, said head enveloping means including outer and inner shells with at least one cavity intermediate said outer and inner shells for receiving and permitting circulation and expansion of coolant fluid, said cavity including means for providing an outlet for coolant fluid, b. an instantaneously activatable coolant fluid source, c. means for providing fluid communication between said coolant fluid source and said head enveloping means, whereby when said coolant fluid source is activated and coolant fluid is introduced into said head enveloping means, said head enveloping means becomes instantaneously chilled, to rapidly transmit this chill to the brain, cooling the brain to a temperature sufficient to slow the metabolism of the brain; and a neck supporting means for cooling the upper spinal column, said neck supporting means provided with means therein for circulation of coolant fluid and separate means for providing fluid communication between said neck supporting means and a coolant fluid source.

11. The apparatus of claim 10, wherein said neck supporting means includes an upwardly curved portion to permit access to vessels of the neck.

12. The apparatus of claim 10, wherein said neck supporting means includes exhaust ports at a lower perimeter.

13. A method for treating ischemic and anoxic brain injuries in mammals, which comprises:

a. placing a means for enveloping a head of a mammal over the head, said head enveloping means resting unsupported on the head, said head enveloping means including outer and inner shells with at least one cavity intermediate said outer and inner shells for receiving and permitting circulation and expansion of coolant fluid, said cavity including a plurality of valveless outlets disposed along a lower back edge portion of said enveloping means;

b. adjusting said head enveloping means; and c. activating an instantaneously activatable external fluid source from an initially inactive state, said external fluid coolant source being in fluid communication with said head enveloping means, whereby chilled fluid is transferred from said external coolant fluid source to said head enveloping means, such that said head enveloping means is instantaneously chilled to a sufficiently low temperature, whereby said chill is transferred to the brain, lowering the metabolism of the brain.

14. The method of claim 13, further comprising placing a neck supporting means with means for circulation of coolant fluid and means for receiving coolant fluid from said head enveloping means under a neck of the mammal and into abutment with said head enveloping means, whereby coolant is passed through said head enveloping means to said neck supporting means for cooling the brain stem and upper spinal column of the mammal to a point where the metabolism of the brain and brain stem is lowered.

15. An apparatus for cooling a brain, comprising:

a. a multiple piece helmet-type element for resting unsupported on a head of the mammal, each of said multiple pieces in fluid communication with each other;

b. said multiple pieces including an outer and inner shell with at least one cavity intermediate said outer and inner shells for receiving and permitting circulation and expansion of coolant fluid;

c. at least one of said multiple pieces including a plurality of valveless outlets for coolant fluid, said plurality of valveless outlets being disposed along a lower back edge portion of said at least one multiple piece and providing communication between the cavity and the ambient atmosphere upon initial introduction of coolant fluid into the cavity;

d. an instantaneously activatable coolant fluid source; and e. means for providing fluid communication between said fluid source and at least one of said multiple pieces of said helmet-type element, whereby when said coolant fluid source is activated and coolant fluid is introduced into at least one of said multiple pieces of said helmet-type element, said multiple pieces become instantaneously chilled, to rapidly transmit the chill to the brain, cooling the brain to a temperature sufficient to slow the metabolism of the brain.

16. An apparatus for cooling a brain comprising:
a. a multiple piece helmet-type element for resting unsupported on a head of the mammal each of said multiple pieces in fluid communication with each other,
b. said multiple pieces including an outer and inner shell with at least one cavity intermediate said outer and inner shells for receiving and permitting circulation and expansion of coolant fluid:
c. at least one of said multiple pieces including means for providing an outlet for coolant fluid:
d. an instantaneously activatable coolant fluid source:
e. means for providing fluid communication between said coolant fluid source and at least one of said multiple pieces of said helmet-type element, whereby when said coolant fluid source is activated and coolant fluid is introduced into at least one of said multiple pieces of said helmet-type element, said multiple pieces become instantaneously chilled, to rapidly transmit the chill to the brain, cooling the brain to a temperature sufficient to slow the metabolism of the brain: and
neck supporting means for cooling the upper spinal column of the neck and back, said neck supporting means provided with means therein for circulation of coolant fluid, and means for providing fluid communication between said multiple piece helmet-type element and neck supporting means, said neck supporting means extending a substantial distance along the upper spinal column, whereby when said coolant fluid source is activated and introduced into said neck supporting means, said neck supporting means becomes instantaneously chilled to rapidly transmit this chill to the upper spinal column at a temperature sufficient to slow the metabolism of the brain.

17. An apparatus for cooling a brain, comprising:
a. a multiple piece helmet-type element for resting unsupported on a head of the mammal, each of said multiple pieces in fluid communication with each other;
b. said multiple pieces including an outer and inner shell with at least one cavity intermediate said outer and inner shells for receiving and permitting circulation and expansion of coolant fluid;
c. at least one of said multiple pieces including means for providing an outlet for coolant fluid;
d. an instantaneously activatable coolant fluid source; and
e. means for providing fluid communication between said fluid source and at least one of said multiple pieces of said helmet-type element, whereby when said coolant fluid source is activated and coolant fluid is introduced into at least one of said multiple pieces of said helmet-type element, said multiple pieces become instantaneously chilled, to rapidly transmit the chill to the brain, cooling the brain to a temperature sufficient to slow the metabolism of the brain, the apparatus additionally including neck supporting means for cooling the upper spinal column, said neck supporting means provided with means therein for circulation of coolant fluid and separate means for providing fluid communication between said neck supporting means and a coolant fluid source.

18. An apparatus for cooling a brain, comprising:
a. means for enveloping a head, said head enveloping means for resting unsupported on the head, said head enveloping means including outer and inner shells with at least one cavity intermediate said outer and inner shells for receiving and permitting circulation and expansion of coolant fluid, said cavity including a plurality of valveless outlets for coolant fluid disposed along a lower back edge portion of said enveloping means;
b. a container comprising a coolant fluid source; and
c. means for providing fluid communication between said fluid source and said head enveloping means, whereby when said coolant fluid source is activated and coolant fluid is introduced into said head enveloping means, said head enveloping means becomes instantaneously chilled, to rapidly transmit this chill to the brain, cooling the brain to a temperature sufficient to slow the metabolism of the brain.

19. A method for reducing or preventing at least one of brain, brain stem and associated nervous tissue injuries to a mammal suffering from a trauma that has or is suspected to have caused an interruption of blood or oxygen flow to the brain, the method comprising:
placing on said mammal's head a helmet that comprises connected outer and inner shells and at least one intermediate cavity extending substantially throughout a width of the helmet between said shells;
introducing coolant fluid into said cavity such that the coolant fluid expands and flows throughout the at least one cavity and thereby substantially throughout the width of the helmet to chill the helmet to a temperature low enough to slow the metabolism of the brain of said mammal; and
continuously allowing exit of the coolant fluid from the helmet, directly to the ambient atmosphere without varying exit of the coolant fluid with a valve through an outlet on said helmet.

20. The method of claim 19, wherein the coolant exits through multiple exhaust ports in the helmet.

21. The method of claim 19, wherein a cross-sectional area through which the coolant fluid exits the helmet is larger than the cross-sectional area through which the coolant fluid was introduced into the helmet.

22. The method of claim 19, wherein the coolant fluid is introduced from a hand-held portable coolant fluid source.

23. The apparatus of claim 19, wherein the inner shell is continuous.

24. The method of claim 21, further comprising activating an external coolant fluid source from an initially inactive state, said external coolant fluid source being in fluid communication with and expanding in said helmet.

25. The method of claim 21, further comprising placing a neck support with at least one cavity for circulation of coolant fluid and at least one port for receiving coolant fluid from said helmet under a neck of the mammal and into abutment with said helmet, whereby coolant fluid is passed through said helmet to said neck support and cools a brain stem and upper spinal column of the mammal to a point where the metabolism of the brain is slowed.

26. A method for reducing or preventing at least one of brain, brain stem and associated nervous tissue injuries to a mammal suffering from a trauma that has or is suspected to have caused an interruption of blood or oxygen flow to the brain, the method comprising:
placing on said mammal's head a portable on-site helmet that comprises connected outer and inner shells and an intermediate cavity extending substantially throughout a width of the helmet between said shells;
introducing a coolant fluid from a coolant source connected with said helmet, wherein no external regulating components other than the coolant fluid source are connected with the helmet; and cooling at least said inner shell to a temperature low enough to slow the metabolism of the brain of said mammal.

27. The method of claim 23, further comprising placing a neck support with at least one cavity for circulation of coolant fluid and at least one port for receiving coolant fluid from said helmet under a neck of the mammal and into abutment with said helmet, whereby coolant fluid is passed through said helmet to said neck support and cools a brain stem and upper spinal column of the mammal to a point where the metabolism of the brain is slowed.

28. The method of claim 23, further comprising activating the coolant fluid source from an initially inactive state, said external coolant fluid source, being in fluid communication with and expanding in said helmet.

29. The method of claim 26, wherein no external monitoring components are connected with the helmet.

30. A method for treating or preventing at least one of brain, brain stem and associated nervous tissue injuries in mammals, which comprises:
   a. covering at least a portion of a head of a mammal with a helmet, said helmet including outer and inner shells with at least one cavity intermediate said outer and inner shells for receiving and permitting circulation of a coolant fluid;
   b. placing a neck support under a neck of the mammal and into abutment with said helmet; and
   c. placing a coolant source in fluid communication with said helmet;
   d. transferring a coolant fluid from said coolant source to said helmet such that said helmet is chilled to a temperature such that at least one of the brain, brain stem and associated nervous tissue of the mammal is cooled to a point where the metabolism of said at least one of the brain, brain stem, and associated nervous tissue, is lowered.

31. The method of claim 30, further including the step of adjusting said helmet for retention on the head.

32. The method of claim 30, further including the step of placing an external coolant source in fluid communication with said neck support.

33. The method of claim 30, wherein said step of transferring a coolant fluid further includes transferring coolant fluid to said neck support.

34. An apparatus for treating or preventing at least one of brain, brain stem and associated nervous tissue injuries in a mammal, comprising a helmet that comprises:
   connected outer and inner shells;
   an intermediate cavity extending substantially throughout a width of the helmet between said shells;
   at least one inlet for introducing a fluid into said intermediate cavity;
   at least one valveless outlet placing an interior of said cavity in continuous direct contact with the ambient atmosphere; and
   a neck support positionable adjacent an upper spinal column of said mammal said neck support including at least one cavity for circulation of coolant fluid and at least one port for fluid communication between said neck support and a coolant fluid source.

35. The apparatus of claim 34, wherein said helmet includes flexible means for adjustment and retention on the head.

36. The apparatus of claim 34, wherein said neck support includes at least one port cooperatively aligned with one of said plurality of valveless outlets of said helmet.

37. The apparatus of claim 34, wherein said neck support includes exhaust ports at a lower perimeter.

38. The apparatus of claim 34, wherein the at least one valveless outlet comprises a plurality of valveless outlets disposed along a lower back edge portion of said outer shell.

39. An apparatus for treating or preventing at least one of brain, brain stem and associated nervous tissue injuries in a mammal, comprising a helmet that comprises:
   connected outer and inner shells; and
   an intermediate cavity extending substantially throughout a width of the helmet between said shells, said cavity being divided into multiple sections along the width of the helmet, each said section being in fluid communication with an adjacent said section through cooperatively aligned ports; and
   a neck support positionable adjacent an upper spinal column of said mammal, said neck support including at least one cavity for circulation of coolant fluid and at least one port for fluid communication between said neck support and a coolant fluid source.

40. The apparatus of claim 39, wherein said inner and outer shells each comprise multiple pieces defining said multiple sections.

41. The apparatus of claim 40, wherein said helmet pieces comprise cooperatively aligned coolant fluid ports at at least one interface between said helmet pieces.

42. The apparatus of claim 39, wherein said helmet includes flexible means for adjustment and retention on the head.

43. The apparatus of claim 39, wherein said neck support includes at least one port cooperatively aligned with one of said plurality of valveless outlets of said helmet.

44. The apparatus of claim 39, wherein said neck support includes exhaust ports at a lower perimeter.

45. Apparatus for cooling at least one of a brain, brain stem and upper spinal column, comprising:
   a. a helmet configured to rest on a head of a mammal free from outside support;
   b. said helmet including outer and inner shells with at least one cavity intermediate said outer and inner shells for receiving coolant fluid, said at least one cavity permitting circulation of a coolant fluid; and
   c. a neck support capable of cooling the upper spinal column of the neck and back of said mammal, said neck support providing circulation of a coolant fluid and fluid communication between said helmet and said neck support;
   d. wherein when coolant fluid is transferred into at least one of said helmet and said neck support, said helmet and/or said neck support is chilled, and rapidly transmits this chill to at least one of the brain, brain stem, associated nervous tissues and upper spinal column, at a temperature sufficient to slow the metabolism of said at least one of the brain, brain stem and associated nervous tissues and upper spinal column.

46. The apparatus of claim 45, which further is adapted to allow fluid communication between said neck support and a coolant source.

47. The apparatus of claim 45, further including cooperatively aligned ports at an interface of said helmet and said neck support.

48. The apparatus of claim 45, wherein said neck support includes an upwardly curved portion to permit access to vessels of the neck.

49. The apparatus of claim 45, wherein said neck support includes at least one exhaust port.

50. The apparatus of claim 45, wherein said at least one exhaust port is located at a perimeter of said neck support.

51. The apparatus of claim 45, wherein said helmet includes at least one exhaust port.

52. An apparatus for treating or preventing at least one of brain, brain stem and associated nervous tissue injuries in a mammal, comprising a helmet that comprises:

connected outer and inner shells;

an intermediate cavity extending substantially throughout a width of the helmet between said shells;

at least one inlet for introducing a fluid into said cavity;

at least one valveless outlet hole placing an interior of said cavity in continuous direct contact with an ambient atmosphere; and a neck support positionable adjacent an upper spinal column of said mammal, said neck support including at least one cavity for circulation of coolant fluid and at least one port for fluid communication between said neck support and a coolant fluid source.

53. An apparatus for treating or preventing at least one of brain, brain stem and associated nervous tissue injuries in a mammal, comprising a helmet that comprises:

connected outer and inner shells;

an intermediate cavity extending substantially throughout a width of the helmet between said shells, said cavity being divided into multiple sections along the width of the helmet, each said section being in fluid communication with an adjacent said section through cooperatively aligned ports; and a neck support positionable adjacent an upper spinal column of said mammal, said neck support including at least one cavity for circulation of coolant fluid and at least one port for communication between said neck support and a coolant fluid source.

54. A method for reducing or preventing at least one of brain, brain stem and associated nervous tissue injuries to a mammal suffering from a trauma that has or is suspected to have caused an interruption of blood or oxygen flow to the brain, the method comprising:

placing on said mammal's head a helmet that comprises connected outer and inner shells and at least one intermediate cavity extending substantially throughout a width of the helmet between said shells and placing a neck support with at least one cavity for circulation of coolant fluid and at least one port for receiving coolant fluid from said helmet under a neck of the mammal and into abutment with the helmet;

introducing coolant fluid into said cavity such that the coolant fluid expands and flows throughout the at least one cavity and thereby substantially throughout the width of the helmet to chill the helmet to a temperature low enough to slow the metabolism of the brain of said mammal, whereby coolant fluid is passed through the helmet to said neck support and cools the brain stem and upper spinal column of the mammal to a point where a metabolism of the brain is slowed; and continuously allowing exit of the coolant fluid to the ambient atmosphere without controlling exit of the coolant fluid with a valve through an outlet on said helmet.

55. An apparatus for treating or preventing at least one of brain, brain stem and associated nervous tissue injuries in a mammal, comprising a helmet that comprises:

connected outer and inner shells, an intermediate cavity extending substantially throughout a width of the helmet between said shells, at least one inlet for introducing a coolant fluid into said intermediate cavity; and a plurality of valveless outlets disposed on the outer shell of the helmet directly adjacent an ambient atmosphere, the valveless outlets placing an interior of said cavity in continuous direct contact with the ambient atmosphere, wherein a cross-sectional area through which the coolant fluid exits the helmet is larger than the cross-sectional area through which coolant fluid was introduced into the helmet.

56. Apparatus for cooling at least one of a brain, brain stem and upper spinal column, comprising:

a. a helmet configured to rest on a head of a mammal free from outside support;

b. said helmet including outer and inner shells with at least one cavity intermediate said outer and inner shells for receiving coolant fluid, said at least one cavity permitting circulation of a coolant fluid; and c. a neck support capable of cooling the upper spinal column of the neck and back of said mammal, said neck support providing circulation of a coolant fluid;

d. wherein when coolant fluid is transferred into at least one of said helmet and said neck support, said helmet and/or said neck support is chilled, and rapidly transmits this chill to at least one of the brain, brain stem, associated nervous tissues and upper spinal column, at a temperature sufficient to slow the metabolism of said at least one of the brain, brain stem and associated nervous tissues and upper spinal column.

\* \* \* \* \*